(12) United States Patent
Ina et al.

(10) Patent No.: US 11,024,030 B2
(45) Date of Patent: Jun. 1, 2021

(54) APPARATUS, METHOD, AND RECORDING MEDIUM

(71) Applicant: YOKOGAWA ELECTRIC CORPORATION, Tokyo (JP)

(72) Inventors: Yukihiro Ina, Tokyo (JP); Hirofumi Sakashita, Tokyo (JP)

(73) Assignee: Yokogawa Electric Corporation, Tokyo (JP)

( * ) Notice: Subject to any disclaimer, the term of this patent is extended or adjusted under 35 U.S.C. 154(b) by 0 days.

(21) Appl. No.: 16/673,982

(22) Filed: Nov. 5, 2019

(65) Prior Publication Data

US 2020/0167927 A1 May 28, 2020

(30) Foreign Application Priority Data

Nov. 28, 2018 (JP) .............................. JP2018-222705

(51) Int. Cl.
*G06T 7/00* (2017.01)
*G06K 9/62* (2006.01)

(52) U.S. Cl.
CPC .......... *G06T 7/0016* (2013.01); *G06K 9/6277* (2013.01); *G06T 2207/20081* (2013.01); *G06T 2207/20084* (2013.01)

(58) Field of Classification Search
CPC ......... G06T 7/0016; G06T 2207/20081; G06T 2207/20084; G06K 9/6277
See application file for complete search history.

(56) References Cited

U.S. PATENT DOCUMENTS

2007/0231921 A1* 10/2007 Roder ..................... A61P 35/00
436/173
2008/0294017 A1* 11/2008 Gobeyn ................. A61B 5/444
600/301

(Continued)

FOREIGN PATENT DOCUMENTS

EP 3293736 A1 3/2018
JP 2012202743 A 10/2012

OTHER PUBLICATIONS

Extended European Search Report for European Patent Application No. 19210312.5, issued by the European Patent Office dated Apr. 21, 2020.

(Continued)

*Primary Examiner* — Khai M Nguyen

(57) ABSTRACT

In a related-art technology, training images in accordance with the number of classifications need to be prepared to perform training process. For this reason, in a case where a model is caused to output how much effect of a drug is expressed, a training image needs to be prepared for each expression degree, and it is troublesome to create the model. Provided is an apparatus including an image obtaining unit configured to obtain an evaluation target image depicting a subject of an evaluation target, a probability obtaining unit configured to obtain a recognition probability regarding the evaluation target image by using a model that outputs, in accordance with input of an image, a recognition probability at which a subject of the image is recognized as the subject before effect of a drug is expressed or the subject after the effect of the drug is expressed, and a calculation unit configured to calculate an expression degree of the effect of the drug based on the recognition probability of the evaluation target image.

8 Claims, 7 Drawing Sheets

(56) References Cited

U.S. PATENT DOCUMENTS

2009/0234626 A1 9/2009 Yu
2016/0196503 A1* 7/2016 Guan ................ G06K 9/00375
706/12

OTHER PUBLICATIONS

Takuya Kano et al, Automatic classification of breast density on CT images by using deep CNN, IEICE Technical Report, vol. 116, No. 39, pp. 21-25.
Karen Simonyan et al, "Very Deep Convolutional Networks for Large-Scale Image Recognition", Published as a conference paper at ICLR 2015, Visual Geometry Group, Department of Engineering Science, University of Oxford, p. 1-p. 14, https://arxiv.org/pdf/1409.1556.pdf.
Office Action for European Patent Application No. 19210312.5, issued by the European Patent Office dated Jan. 15,2021.
Office Action issued for counterpart Japanese Application No. 2018-222705, issued by the Japan Patent Office dated Feb. 24, 2021 (drafted on Feb. 15, 2021).

* cited by examiner

APPARATUS, METHOD, AND RECORDING MEDIUM

The contents of the following Japanese patent application(s) are incorporated herein by reference:

2018-222705 filed in JP on Nov. 28, 2018.

BACKGROUND

1. Technical Field

The present invention relates to an apparatus, a method, and a recording medium.

2. Related Art

Up to now, various technologies for performing classification of a subject by using a pre-trained model have been proposed. For example, according to a technology described in NPL 1, an evaluation target image is classified into any one of four types by using a model where training process has been performed using the four types of images classified in accordance with a breast density.

NPL 1 "Automatic classification of breast density on CT images by using deep CNN", Takuya Kano, Xiangrong Zhou, Hiromi Koyasu, Ryuziro Yokoyama, Takeshi Hara, Masayuki Matsuo, Hiroshi Fujita, IEICE Technical Report, Vol. 116, No. 39, pp. 21-25

However, according to the technology, training images in accordance with the number of classifications need to be prepared to perform training process. For this reason, in a case where a model is caused to output how much effect of a drug is expressed, a training image needs to be prepared for each expression degree, and it is troublesome to create the model.

SUMMARY

To address the above-mentioned problem, according to a first aspect of the present invention, an apparatus is provided. The apparatus may include an image obtaining unit configured to obtain an evaluation target image depicting a subject of an evaluation target. The apparatus may include a probability obtaining unit configured to obtain a recognition probability regarding the evaluation target image by using a model that outputs, in accordance with input of an image, a recognition probability at which a subject of the image is recognized as the subject before effect of a drug is expressed or the subject after the effect of the drug is expressed. The apparatus may include a calculation unit configured to calculate an expression degree of the effect of the drug based on the recognition probability of the evaluation target image.

The probability obtaining unit may obtain the recognition probability regarding each of a plurality of the evaluation target images depicting the subjects to which the drug is administrated under different administration conditions. The calculation unit may calculate the expression degree of the evaluation target image based on the recognition probability of each of the plurality of evaluation target images.

The apparatus may include an administration condition obtaining unit configured to obtain administration conditions of the drug with respect to the subjects of the respective evaluation target images. The apparatus may include a detection unit configured to detect an administration condition under which the expression degree becomes a predetermined summary statistic based on the expression degrees of the respective evaluation target images and the administration conditions corresponding to the respective evaluation target images.

The probability obtaining unit may obtain the recognition probability regarding each of the plurality of evaluation target images depicting the subjects to which the drug is administrated under a uniform administration condition. The calculation unit may calculate the expression degree based on a representative value of a plurality of the recognition probabilities regarding the plurality of evaluation target images.

The probability obtaining unit may obtain the recognition probability regarding each of the plurality of evaluation target images depicting the subjects to which the drug is administrated under a uniform administration condition. The calculation unit may calculate the expression degree based on a variance of a plurality of the recognition probabilities regarding the plurality of evaluation target images.

The calculation unit may include a conversion unit configured to convert the recognition probability regarding the evaluation target image into the expression degree.

The apparatus may include a training data obtaining unit configured to obtain training data including a pre-expression image depicting the subject before the effect of the drug is expressed and a post-expression image depicting the subject after the effect of the drug is expressed. The apparatus may include a training processing unit configured to execute training process of the model by using the training data.

The pre-expression image may be an image depicting the subject before the drug is administrated. The post-expression image may be an image depicting the subject after the effect of the drug is expressed to a maximum extent.

According to a second aspect of the present invention, a method is provided. The method may include obtaining an evaluation target image depicting a subject of an evaluation target. The method may include obtaining a recognition probability regarding the evaluation target image by using a model that outputs, in accordance with input of an image, a recognition probability at which a subject of the image is recognized as the subject before effect of a drug is expressed or the subject after the effect of the drug is expressed. The method may include calculating an expression degree of the effect of the drug based on the recognition probability of the evaluation target image.

According to a third aspect of the present invention, a recording medium recording a program is provided. The program may cause a computer to execute obtaining an evaluation target image depicting a subject of an evaluation target. The program may cause the computer to execute obtaining a recognition probability regarding the evaluation target image by using a model that outputs, in accordance with input of an image, a recognition probability at which a subject of the image is recognized as the subject before effect of a drug is expressed or the subject after the effect of the drug is expressed. The program may cause the computer to execute calculating an expression degree of the effect of the drug based on the recognition probability of the evaluation target image.

It is noted that not all the features necessary for the present invention are enumerated in the above-mentioned summary of the invention. In addition, sub-combinations of these feature groups may also constitute the invention.

DESCRIPTION OF EXEMPLARY EMBODIMENTS

Hereinafter, the present invention will be described by way of embodiments of the invention, but the following embodiments are not intended to restrict the invention in accordance with the scope of claims. In addition, not all combinations of features described in the embodiments necessarily have to be essential to solving means of the invention.

1. Configuration of Apparatus 1

Figure 1:
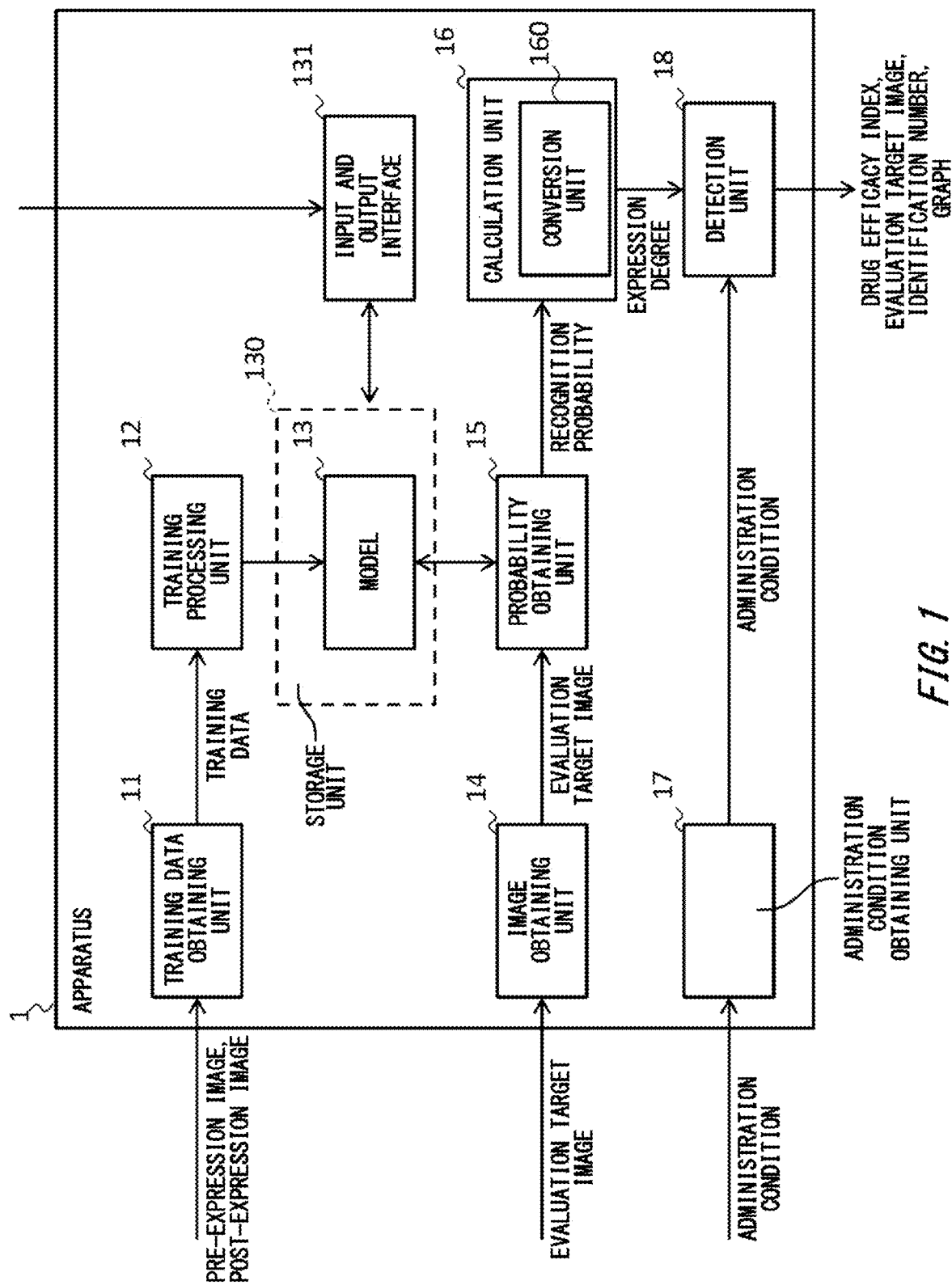
FIG. 1 illustrates an apparatus 1 according to the present embodiment.

FIG. 1 illustrates an apparatus 1 according to the present embodiment. The apparatus 1 is configured to perform an analysis on drug efficacy by using a model 13 where training process has been performed. The apparatus 1 includes a training data obtaining unit 11, a training processing unit 12, the model 13, an image obtaining unit 14, a probability obtaining unit 15, a calculation unit 16, an administration condition obtaining unit 17, and a detection unit 18.

1.1. Training Data Obtaining Unit 11

The training data obtaining unit 11 obtains training data including a pre-expression image depicting a subject before effect of a drug is expressed and a post-expression image depicting the subject after the effect of the drug is expressed. Herein, the subject may be an organ, a tissue, a cell, a cell organelle (in one example, a nucleus), an organic substance (in one example, protein or nucleic acid), or the like of a living matter and may be collected from a living body. The drug has effect with respect to the subject. The effect of the drug is an action for the drug to change the subject where the subject may also be changed to a healthy state or may also be changed to an abnormal state (in one example, a destroyed state).

The training data obtaining unit 11 may obtain image data of the pre-expression image and the post-expression image from a storage device that is not illustrated in the drawing. The training data obtaining unit 11 supplies the pre-expression image and the post-expression image thus obtained to the training processing unit 12 as training data.

1.2. Training Processing Unit 12

The training processing unit 12 executes training process of the model 13 by using the training data. For example, the training processing unit 12 may perform the training process using a deep learning technique.

1.3. Model 13

In accordance with input of an image, the model 13 outputs a recognition probability at which a subject of the image is recognized as the subject before the effect of the drug is expressed or as the subject after the effect of the drug is expressed. Herein, the probability is a degree to which the phenomenon is expected to happen and is a percentile such as 40% according to the present embodiment in one example, but may also be a ratio such as 0.4.

The model 13 may be generated by the training process by the training processing unit 12. According to the present embodiment, in one example, the model 13 may be a convolutional neural network (CNN) or VGG. VGG refers to a model developed by Visual Geometry Group, Department of Engineering Science, University of Oxford and is a model disclosed, for example, in "VERY DEEP CONVOLUTIONAL NETWORKS FOR LARGE-SCALE IMAGE RECOGNITION", Karen Simonyan, et al., (ICLR 2015, https://arxiv.org/pdf/1409.1556.pdf.).

The model 13 includes a neuron for outputting a probability at which an input image is an image before the effect is expressed and a neuron for outputting a probability at which the input image is an image after the effect is expressed in an output layer, and the model 13 may output probabilities totaling 100(%) from the two output neurons.

The model 13 may be stored in a storage unit 130 inside the apparatus 1. The model 13 may be output to the outside of the apparatus 1 via an input and output interface 131. The model 13 may be set from the outside via the input and output interface 131.

1.4. Image Obtaining Unit 14

The image obtaining unit 14 obtains one or more evaluation target images depicting a subject of an evaluation target. The subject of the evaluation target is a subject where an expression degree of the effect of the drug is to be evaluated. The expression degree of the effect of the drug refers to a degree to which the subject is changed due to the effect of the drug. In one example, the subject of the evaluation target may be a subject to which the drug is administrated under a predetermined administration condition. In one example, the administration condition may also be a dose of the drug or may also be a time for which the subject is exposed in a state where the effect of the drug is expressed (which may also be referred to as an exposure time).

It is noted that, in other words, the exposure time is an elapsed time from when the drug is administrated until when imaging of the subject is performed. In a case where a plurality of evaluation target images are obtained, the administration conditions of the drug may also be varied between these or may also be uniform. Varied administration conditions may indicate that at least one of the dose of the drug and the exposure time is varied. Uniform administration condition may indicate that both the dose of the drug and the exposure time are uniform.

The image obtaining unit 14 may obtain image data of the evaluation target images from a storage device that is not illustrated in the drawing. In this storage device, the administration conditions of the drug with respect to the subjects may be stored while being associated with the image data of the respective evaluation target images. The image obtaining unit 14 supplies the obtained evaluation target images to the probability obtaining unit 15.

1.5. Probability Obtaining Unit 15

The probability obtaining unit 15 obtains recognition probabilities regarding the respective evaluation target images by using the model 13. For example, the probability obtaining unit 15 obtains a recognition probability output by the model 13 in accordance with supply of the image data of the evaluation target image to the model 13, that is, a probability at which the evaluation target image is recognized as the evaluation target image before the effect of the drug is expressed or after the effect of the drug is expressed.

In a case where a plurality of evaluation target images are obtained by the image obtaining unit 14, the probability obtaining unit 15 may obtain a recognition probability regarding each of the plurality of these evaluation target images. The probability obtaining unit 15 supplies the obtained recognition probabilities to the calculation unit 16.

1.6. Calculation Unit 16

The calculation unit 16 calculates an expression degree of the effect with respect to the subject of the evaluation target based on the recognition probability of the evaluation target image.

The calculation unit 16 may include a conversion unit 160 that converts the recognition probability regarding the evaluation target image into an expression degree of the effect. The conversion unit 160 may convert the recognition probability into the expression degree by using a previously set function. The function may be set by obtaining a recognition probability of the model 13 with respect to the image by previously using samples of a plurality of subjects and an expression degree specified by an operator, and approximating a relationship between those. In one example, the function may also be an exponential function or a sigmoidal function.

In a case where the recognition probabilities of the plurality of evaluation target images are obtained by the probability obtaining unit 15, the calculation unit 16 may calculate, based on the recognition probabilities of the plurality of respective evaluation target images, the expression degrees of the evaluation target images. That is, the calculation unit 16 may calculate the expression degree based on the recognition probability for each evaluation target image. The calculation unit 16 supplies the calculated expression degrees to the detection unit 18. It is noted that the calculation unit 16 may also output the expression degrees to the outside of the apparatus 1.

1.7. Administration Condition Obtaining Unit 17

The administration condition obtaining unit 17 obtains the administration condition of the drug with respect to the subject of the evaluation target image. For example, in a case where a plurality of evaluation target images are obtained by the image obtaining unit 14, the administration condition obtaining unit 17 may respectively obtain the administration conditions of the drug with respect to those subjects. The administration condition obtaining unit 17 may obtain the administration conditions of the drug from the storage device that stores the evaluation target images and the administration conditions of the drug in association with each other. Instead of this, the administration condition obtaining unit 17 may also obtain administration conditions regarding the respective evaluation target images from the operator. The administration condition obtaining unit 17 supplies the obtained administration conditions to the detection unit 18.

1.8. Detection Unit 18

The detection unit 18 detects an administration condition under which (also referred to as a drug efficacy index) the expression degree becomes a predetermined summary statistic (also referred to as an established summary statistic) based on the expression degrees of the respective evaluation target images and the administration conditions corresponding to the respective evaluation target images. For example, in a case where a plurality of evaluation target images where the administration conditions of the drug are varied are obtained by the image obtaining unit 14, the detection unit 18 may detect the drug efficacy index based on the expression degrees and the administration conditions of those.

Herein, the summary statistic may be a value indicating characteristics of a sample distribution representatively (in summary), and may be an average value, a median value, a highest value, a lowest value, or the like in one example. According to the present embodiment, in one example, the established summary statistic may be a value that is half of the highest value of the expression degree, that is, EC (half maximal Effective Concentration) 50 or IC (half maximal Inhibitory Concentration) 50. According to this, the drug efficacy index indicating EC50 or IC50 is detected. The detection unit 18 outputs the detected drug efficacy index to the outside of the apparatus 1. The evaluation target image corresponding to the detected drug efficacy index or an identification number thereof may also further be output. The detection unit 18 may also further output a graph representing a relationship between the administration conditions of the respective evaluation target images and the expression degrees together with the detected drug efficacy index.

In accordance with the apparatus 1 described above, since the expression degree of the effect is calculated based on the recognition probability at which the subject of the evaluation target image is recognized as the subject before the effect is expressed or after before the effect is expressed, when the training process of the model 13 is performed by using the training data including the images before and after the effect is expressed, it becomes possible to obtain the expression degree of the evaluation target image. Herein, in order to cause the model 13 to output the expression degree of the evaluation target image, it is also conceivable to perform the training process by preparing a training image for each expression degree.

In contrast to this, in the apparatus 1 according to the present embodiment, an appropriate expression degree during a period between a time before the effect is expressed and a time after the effect is expressed can be output as the expression degree of the evaluation target image by using the images before and after the effect is expressed for the training process of the model 13. Therefore, as compared with a case where the training process is performed using the training data including the image for each expression degree of the effect, it is possible to easily create the model 13 and obtain the expression degree of the effect regarding the evaluation target image.

It is noted that, in order to obtain an image from the expression degree of the evaluation target image, it is also considerable to detect a feature amount of the image by image processing to be converted into the expression degree of the effect (for example, Japanese Unexamined Patent Application Publication No. 2009-63509), but it is troublesome to create an image processing program or adjust an algorithm or a parameter for each image, which places a burden on a user.

In addition, since the recognition probability is converted into the expression degree, understanding of the expression degree can be facilitated as compared with a case where the recognition probability is directly used as the expression degree.

In addition, since the plurality of evaluation target images depicting the subjects to which the drug is administrated under the different administration conditions are obtained, and the expression degrees regarding the plurality of administration conditions are calculated, it is possible to obtain the relationship between the administration conditions of the drug and the expression degrees.

In addition, since the drug efficacy index in which the expression degree becomes the established summary statistic (in one example, EC50 or IC50) is detected based on the expression degrees of the effect regarding the respective evaluation target images and the administration conditions of the drug, it is possible to obtain a preferable administration condition of the drug.

2. Operation of Apparatus 1

2.1. Training Process

Figure 2:
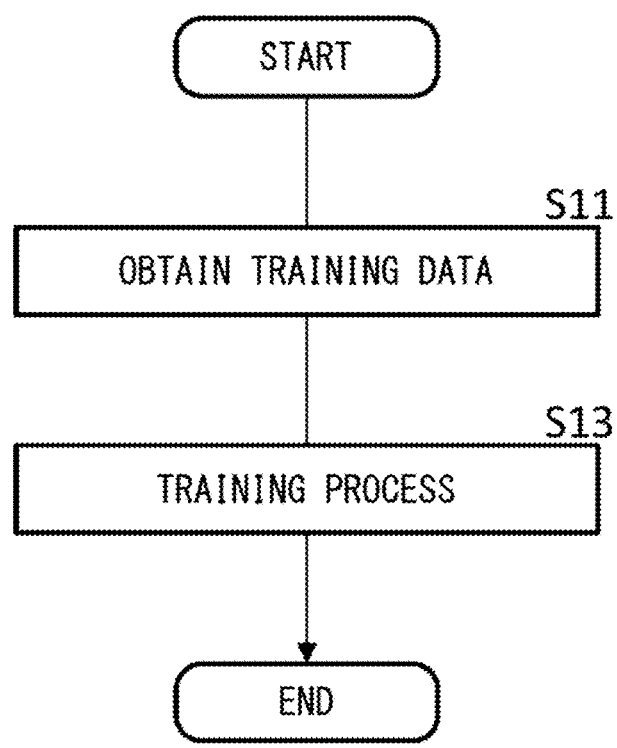
FIG. 2 illustrates training process by the apparatus 1.

FIG. 2 illustrates training process by the apparatus 1. The apparatus 1 performs the training process of the model 13 by performing processing in steps S11 to S13.

In step S11, the training data obtaining unit 11 obtains the training data including the pre-expression image and the post-expression image. Herein, the pre-expression image may be an image depicting the subject before the drug is administrated. For example, the pre-expression image may be an image depicting the subject in a state where the drug is not administrated. Instead of this, the pre-expression image may also be an image depicting the subject after the drug is administrated, and for example, may also be an image depicting the subject in a state where the drug is administrated, and the effect is not expressed. In this case, the pre-expression image may be an image classified by the operator as the image before the effect is expressed, and in one example, may also be an image of the subject in which the dose of the drug is lower than a first reference amount, or may also be an image of the subject in which the exposure time is shorter than a first reference time.

In addition, the post-expression image may be an image depicting the subject in a state where the effect of the drug is expressed to a maximum extent. For example, the post-expression image may be an image of the subject under an administration condition where no changes are observed even when the dose of the drug and the exposure time are increased. Instead of this, the post-expression image may also be an image depicting the subject in a state where the drug is administrated, and expression of the effect has been completed irrespective of whether or not the effect is expressed to the maximum extent. In this case, the post-expression image may be an image classified by the operator as the image after the effect is expressed, and in one example, may also be an image of the subject in which the dose of the drug is higher than a second reference amount, and the exposure time is longer than a second reference time.

It is noted that the second reference amount may be higher than the first reference amount, and the first reference time may be longer than a second reference time. These pre-expression image and post-expression image may also be images captured by a microscope (in one example, an optical microscope or an electron microscope), or may also be images captured by other imaging means. According to the present embodiment, in one example, the pre-expression image and the post-expression image are images obtained by capturing a cell serving as the subject which is contained in a well of a microplate by the optical microscope.

In step S13, the training processing unit 12 executes the training process of the model 13 by using the training data. In one example, a training processing unit 12 may perform training process using a deep learning technique. The training processing unit 12 may execute the training process by adjusting a weight of an edge that connects nodes of the model 13 with each other and a bias value of an output node. The processing in steps S11 to S13 may be repeated until accuracy of image recognition by the model 13 sufficiently converges.

In accordance with the above-mentioned operation, since the training process is performed by using the pre-expression image depicting the subject before the drug is administrated and the post-expression image depicting the subject in a state where the expression of the effect of the drug has been completed, an image in which the effect is being expressed halfway through is not used for the training process. Therefore, the training process can be accelerated as compared with a case where the training process is performed by including data in which the effect is being expressed halfway through in the training data.

2.2. Analysis Process

Figure 3:
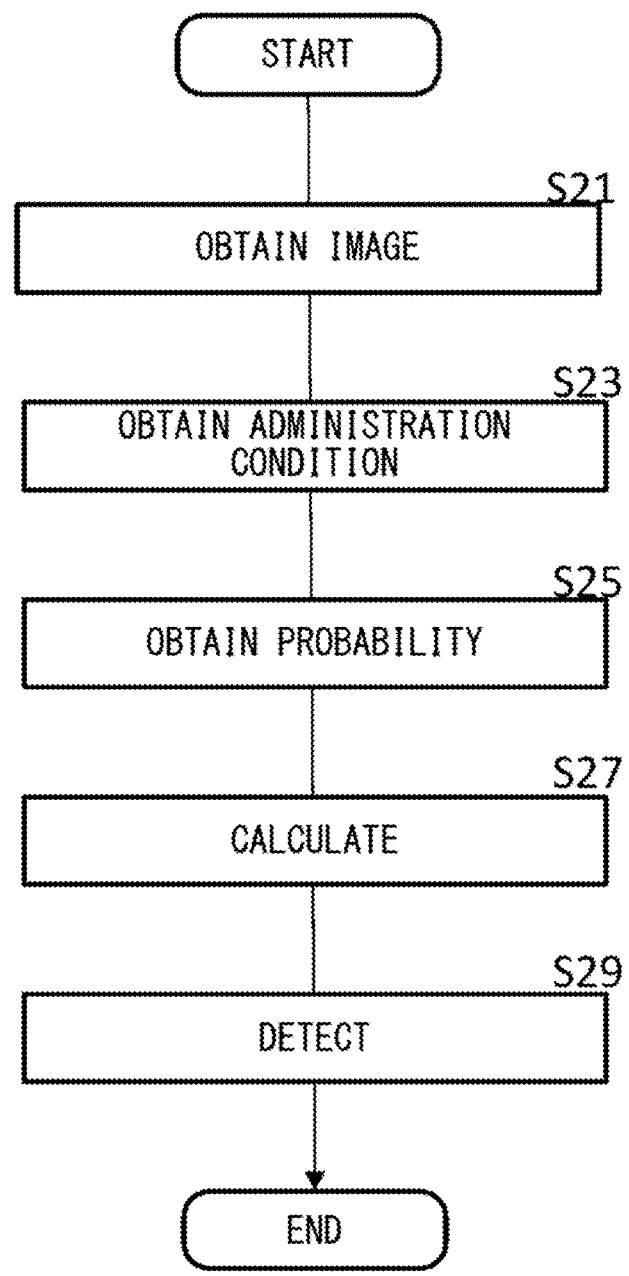
FIG. 3 illustrates analysis process by the apparatus 1.

FIG. 3 illustrates analysis process by the apparatus 1. The apparatus 1 performs processing in steps S21 to S29 to perform an analysis on the drug efficacy by using the model 13 where the training process has been performed.

In step S21, the image obtaining unit 14 obtains the evaluation target image depicting the subject of the evaluation target. For example, the image obtaining unit 14 obtains a plurality of evaluation target images.

According to the present embodiment, in one example, the image obtaining unit 14 obtains a plurality of evaluation target images depicting the subjects to which the drug is administrated under the different administration conditions. For example, the image obtaining unit 14 may also obtain a series of evaluation target images obtained by sequentially increasing the dose amount, or may also obtain a series of evaluation target images obtained by sequentially lengthening the exposure time. A series of these evaluation target images may include an image depicting the subject in a state where the effect of the drug is not expressed and an image depicting the subject in a state where the effect of the drug is expressed to the maximum extent.

In addition, the image obtaining unit 14 obtains a plurality of evaluation target images depicting the subjects to which the drug is administrated under the uniform administration condition. For example, the image obtaining unit 14 obtains a plurality of evaluation target images for each administration condition. In one example, the image obtaining unit 14 may obtain a plurality of images captured in different fields of view in the same well of the microplate or wells under the same administration condition, as the plurality of evaluation target images corresponding to the uniform administration condition.

The evaluation target image may be an image of the same type as the pre-expression image and the post-expression image, and may also be an image captured by a microscope (in one example, an optical microscope or an electron microscope), or may also be an image captured by other imaging means. According to the present embodiment, in one example, the evaluation target image is an image obtained by capturing the cell serving as the subject which is contained in the well of the microplate by the optical microscope.

In step S23, the administration condition obtaining unit 17 obtains the administration conditions of the drug with respect to the subjects of the respective evaluation target images. The processing in step S23 may also be performed before the processing in step S21 or may also be performed between step S25 and step S29.

In step S25, the probability obtaining unit 15 obtains the recognition probability regarding the evaluation target image, for example, the probability of being recognized as the evaluation target image after the effect of the drug is expressed by using the model 13. According to the present embodiment, in one example, the probability obtaining unit 15 obtains the recognition probability regarding each of the plurality of evaluation target images obtained by the image obtaining unit 14.

In step S27, the calculation unit 16 calculates the expression degree of the effect of the drug based on the recognition probability of the evaluation target image. For example, the calculation unit 16 may calculate an expression degree of the plurality of evaluation target images based on a representative value (in one example, an average value, a median value, or a mode value) of the plurality of recognition probabilities regarding the plurality of evaluation target images depicting the subjects to which the drug is administrated under the uniform administration condition. That is, the calculation unit 16 may calculate the expression degree of the evaluation target images for each administration condition. The calculation unit 16 may convert the recognition probability regarding the plurality of evaluation target images (in one example, the average value of the recognition probabilities regarding the plurality of evaluation target images depicting the subjects to which the drug is administrated under the uniform administration condition) into the expression degree of the effect by using the conversion unit 160. In one example, the conversion unit 160 may convert a recognition probability in percentage terms into an expression degree between 0 and 1.

In step S29, the detection unit 18 detects the drug efficacy index in which the expression degree becomes the established summary statistic (according to the present embodiment, EC50 or IC50 in one example) based on the expression degrees of the respective evaluation target images and the administration conditions corresponding to the respective evaluation target images. For example, the detection unit 18 may detect the administration condition corresponding to the expression degree closest to the established summary statistic among the expression degrees of the evaluation target images for each administration condition, as the drug efficacy index. The detection unit 18 may also further output the evaluation target image corresponding to the drug efficacy index or an identification number of the image or the well together with the detected drug efficacy index. The detection unit 18 may output a graph representing a relationship between the administration conditions of the respective evaluation target images and the expression degrees together with the detected drug efficacy index.

It is noted that, in a case where the operator can understand a correspondence relationship between the evaluation target images and the administration conditions thereof (in one example, a case where the correspondence relationship is stored in the storage device), the detection unit 18 may also output a graph representing a relationship between identification numbers of the respective evaluation target images and the expression degrees. Similarly, in a case where the operator can understand a correspondence relationship between the wells where the evaluation target images are captured and the administration conditions of the drug with respect to the wells, the detection unit 18 may also output a graph representing a relationship between identification numbers of the respective wells and the expression degrees.

In accordance with the above-mentioned operation, since the expression degree is calculated based on the representative value of the plurality of recognition probabilities regarding the plurality of evaluation target images under the uniform administration condition of the drug, it is possible to obtain the appropriate expression degree in a case where the recognition probability fluctuates among the evaluation target images under the uniform administration condition.

In addition, since the graph representing the relationship between the administration conditions of the evaluation target images and the expression degrees is output, it is easily understand the relationship between the administration conditions and the expression degrees.

3. Operation Example

Figure 4:
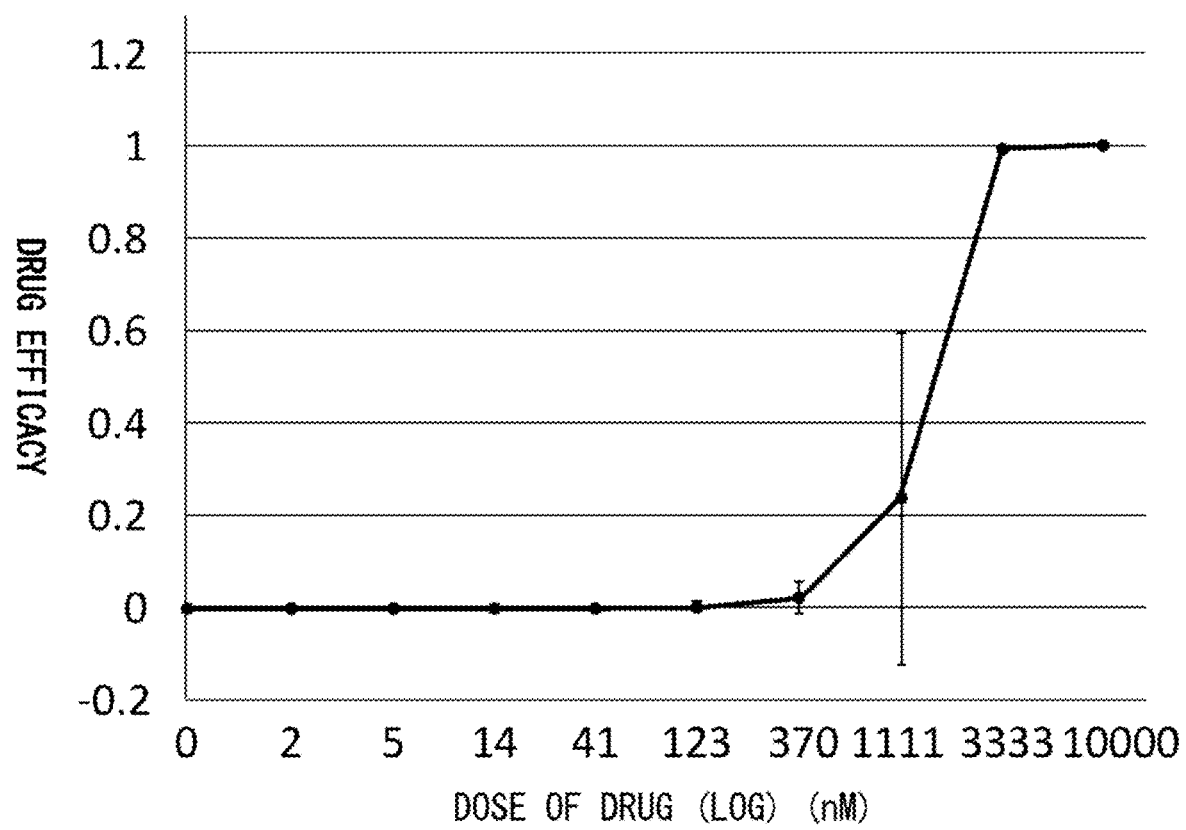
FIG. 4 illustrates a relationship between a dose of a drug and an expression degree.

FIG. 4 illustrates a relationship between the dose of the drug and the expression degree. A horizontal axis in the drawing represents the dose of the drug (nM in one example according to the present embodiment) in log terms. It is noted that the horizontal axis may also be the exposure time of the drug. A vertical axis in the drawing represents the expression degree of the effect of the drug. A plot and an error bar in the drawing indicate an average value and a variance of the expression degrees of the effect regarding a plurality of evaluation target images (for example, 25 to 49 images) which are captured in the wells at the same dose amount. In this example, the dose amount at the dose amount 1111 nM corresponding to the expression degree 0.23 closest to the established summary statistic (in the present operation example, the expression degree 0.5 in one example) among the expression degrees of the effect for each dose amount is detected as the drug efficacy index.

Figure 5:
FIG. 5 illustrates a pre-expression image.

FIG. 5 illustrates the pre-expression image. In this drawing, in one example, the pre-expression image depicts a subject in a state where a drug for degrading fibrous cytoplasm (white parts in the drawing) is not administrated.

Figure 6:
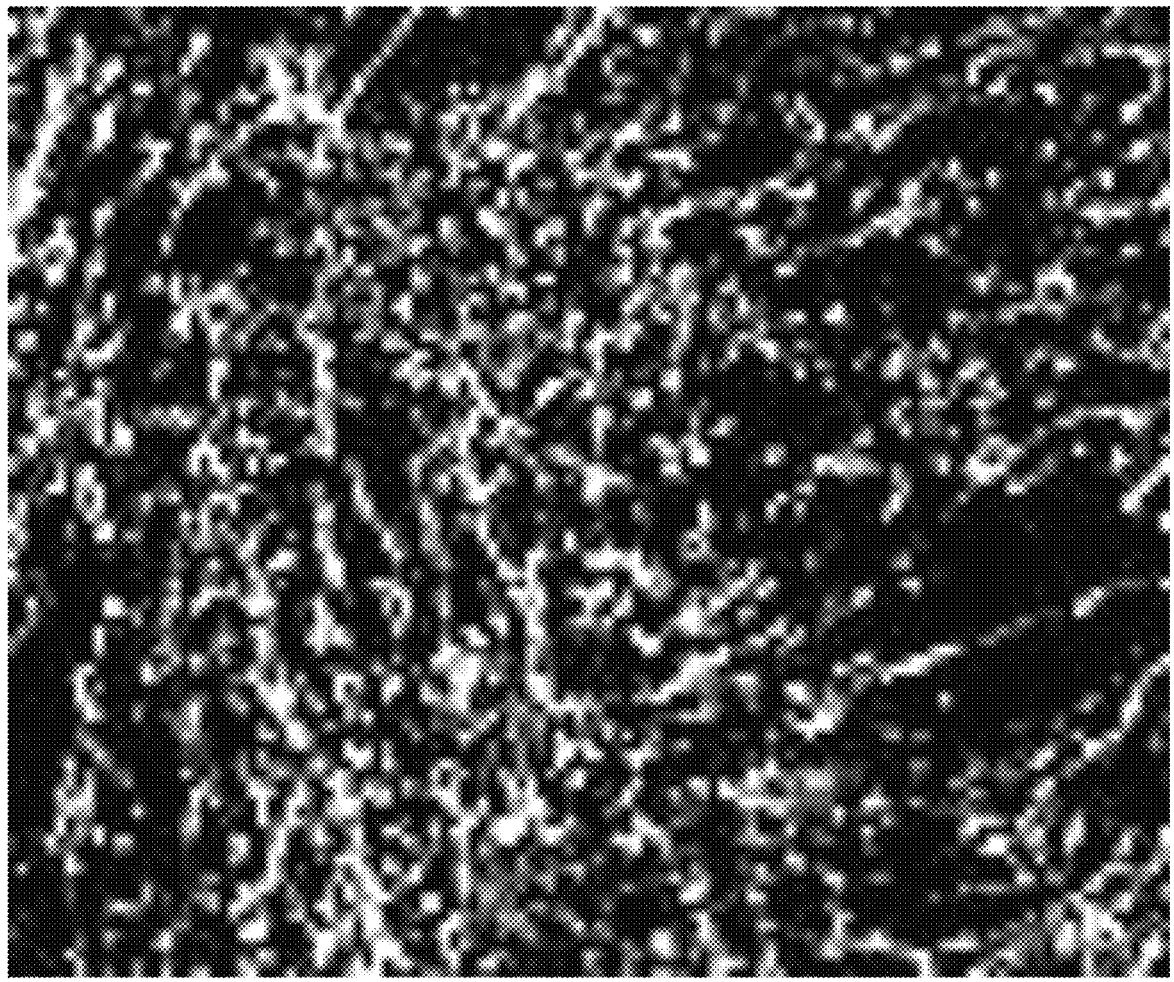
FIG. 6 illustrates a post-expression image.

FIG. 6 illustrates the post-expression image. In this drawing, in one example, the post-expression image depicts a subject in a state where the cytoplasm is degraded to a maximum extent by the effect of the drug.

4. Modified Example

It is noted that, according to the above-mentioned embodiment, it has been described that the apparatus 1 includes the training data obtaining unit 11, the training processing unit 12, the model 13, the administration condition obtaining unit 17, and the detection unit 18, but it may also be sufficient when at least one of these is not included. For example, in a case where the training process of the model 13 is not performed, the apparatus 1 does not need to include the training data obtaining unit 11 and the training processing unit 12. In addition, in a case where the drug efficacy index in which the expression degree becomes the established summary statistic is not detected, the apparatus 1 does not need to include the administration condition obtaining unit 17 and the detection unit 18. In addition, the model 13 may also be stored in a server in the outside of the apparatus 1.

In addition, it has been described that while the drug expresses the effect in one stage, the model 13 outputs the probability at which the evaluation target image is recognized as the post-expression image (or the pre-expression image) of the effect, and the calculation unit 16 calculates the expression degree of the effect. However, in a case where the drug expresses effects in stages (in one example, a case where the subject is expanded in a first stage, and the subject is destroyed in a second stage or the like), the model 13 may output probabilities at which the evaluation target images are recognized as the post-expression images (or the pre-expression images) of the effects in the respective stages.

In addition, the calculation unit 16 may also calculate the expression degree of the effect in at least one stage. In this case, regarding a series of evaluation target images obtained by sequentially increasing the dose of the drug or the exposure time, the calculation unit 16 may normalize the recognition probabilities from the probability obtaining unit 15 or the expression degrees themselves which are calculated by the calculation unit 16 such that the expression degrees of the effects in the respective stages fall within a range from 0 to 1.

For example, in a case where the drug expresses effects in n stages (where n is a natural number higher than or equal to 2), n recognition probabilities from a recognition probability $P_1$ as the post-expression image (or the pre-expression image) of the effect in the first stage up to a recognition probability $P_n$ as the post-expression image (or the pre-expression image) of the effect in an n-th stage may be obtained. In this case, the calculation unit 16 may perform normalization using the recognition probabilities $P_1$ to $P_n$. According to this, in a case where the effects are expressed in a plurality of stages, it is possible to easily understand in which stage the effect is expressed.

In one example, the calculation unit 16 may also normalize the recognition probabilities from the probability obtaining unit 15 or the expression degrees themselves which are calculated by the calculation unit 16 such that the expression degree with respect to all the effects, in other words, the expression degree with respect to the eventual effect falls within the range from 0 to 1. For example, the calculation unit 16 may perform normalization such that the expression degree becomes 0 in a case where the recognition probabilities as the post-expression images of the effects in the respective stages in the effects in all the n stages are respectively 0% (or a value below 0%), and the expression degree becomes 1 in a case where the recognition probability as the post-expression image of the effect in the n-th stage is 100% (or a value exceeding 100%). In this case, the calculation unit 16 may calculate the expression degree regarding only the highest recognition probability among the recognition probabilities as the post-expression images in the plurality of stages. In one example, a case will be described where the recognition probability $P_N$ as the post-expression image in an N-th stage (where N is a natural number satisfying 1≤N≤n) is the highest. In a case where the administration condition (in one example, the dose or the exposure time) under which the expression of the effect in the n-th stage is completed is set as 100, the calculation unit 16 may respectively obtain a percentage $Q_{N\_START}$ of the administration condition under which the expression of the effect in the N-th stage is started and a percentage $Q_{N\_END}$ of the administration condition under which the expression is completed. In one example, $Q_{N\_START}$ may be 100N/n–100/2n (%), and $Q_{N\_END}$ may be set as 100N/n+100/2n (%). The calculation unit 16 may calculate the expression degree of the effect as $(Q_{N\_START}+(Q_{N\_END}-Q_{N\_START})\times P_N)\times 100$.

In addition, it has been described that the calculation unit 16 calculates the expression degree of the effect by converting the recognition probability of the evaluation target image using the function, but the recognition probability may be set as the expression degree of the effect as it is.

In addition, it has been described that the calculation unit 16 calculates the expression degree based on the representative value of the plurality of recognition probabilities regarding the plurality of evaluation target images under the uniform administration condition of the drug, but in addition to this or instead of this, the expression degree may also be calculated based on the variance of the plurality of recognition probabilities. In one example, the calculation unit 16 may set the variance itself as the expression degree. In this case, the detection unit 18 detects the administration condition under which the variance becomes the highest as the drug efficacy index. For example, in the case of the above-described example in FIG. 4, the detection unit 18 may detect the condition at the dose amount 1111 nM of the drug under which the variance becomes the highest, as the drug efficacy index. According to this, it is possible to detect the administration condition under which the effect of the drug may be expressed, that is, the administration condition under which the drug starts to be effective in a case where at least one of the dose amount and the exposure time is sequentially increased.

In addition, it has been described that the training processing unit 12 executes the training process of the model 13 by using the pre-expression image and the post-expression image of one drug, but the training process may also be executed by respectively using pre-expression images and post-expression images of a plurality of drugs. In this case, in accordance with input of the evaluation target image, the model 13 may output recognition probabilities of being recognized as the evaluation target image after the effects of the respective drugs are expressed (or before the effects are expressed).

In addition, the calculation unit 16 may calculate the expression degrees of the effects of the respective drugs based on the recognition probabilities of the evaluation target image regarding the respective drugs. In one example, in a case where the model 13 outputs the recognition probabilities of being recognized as the evaluation target image after the respective effects of the two drugs are expressed, the calculation unit 16 may respectively calculate the expression degree of the effect regarding one of the drugs and the expression degree of the effect regarding the other drug.

In addition, it has been described that the analysis process is performed after the training process of the model 13 is ended, but the training process may also further be performed with respect to the model 13 by using a result of the analysis process. For example, the training data obtaining unit 11 may obtain the evaluation target image set as the evaluation target image before the effect is expressed or after the effect is expressed at a recognition probability higher than or equal to a reference value by the analysis process, as the pre-expression image or the post-expression image.

In addition, the training processing unit 12 may perform the training process by using the training data including the thus obtained image.

Various embodiments of the present invention may be described with reference to flowcharts and block diagrams whose blocks may represent (1) steps of processes in which operations are performed or (2) units of apparatuses responsible for performing operations. Certain steps and units may be implemented by dedicated circuitry, programmable circuitry supplied with computer-readable instructions stored on computer-readable media, and/or processors supplied with computer-readable instructions stored on computer-readable media. Dedicated circuitry may include digital and/or analog hardware circuits and may include integrated circuits (IC) and/or discrete circuits. Programmable circuitry may include reconfigurable hardware circuits comprising logical AND, OR, XOR, NAND, NOR, and other logical operations, flip-flops, registers, memory elements, etc., such as field-programmable gate arrays (FPGA), programmable logic arrays (PLA), etc.

Computer-readable media may include any tangible device that can store instructions for execution by a suitable device, such that the computer-readable medium having instructions stored therein comprises an article of manufacture including instructions which can be executed to create means for performing operations specified in the flowcharts or block diagrams. Examples of computer-readable media may include an electronic storage medium, a magnetic storage medium, an optical storage medium, an electromagnetic storage medium, a semiconductor storage medium, etc. More specific examples of computer-readable media may include a floppy disk, a diskette, a hard disk, a random access memory (RAM), a read-only memory (ROM), an erasable programmable read-only memory (EPROM or Flash memory), an electrically erasable programmable read-only memory (EEPROM), a static random access memory (SRAM), a compact disc read-only memory (CD-ROM), a digital versatile disk (DVD), a BLU-RAY (registered trademark) disc, a memory stick, an integrated circuit card, etc.

Computer-readable instructions may include assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, JAVA (registered trademark), C++, etc., and conventional procedural programming languages, such as the "C" programming language or similar programming languages.

Computer-readable instructions may be provided to a processor of a general purpose computer, special purpose computer, or other programmable data processing apparatus, or to programmable circuitry, locally or via a local area network (LAN), wide area network (WAN) such as the Internet, etc., to execute the computer-readable instructions to create means for performing operations specified in the flowcharts or block diagrams. Examples of processors include computer processors, processing units, microprocessors, digital signal processors, controllers, microcontrollers, etc.

Figure 7:
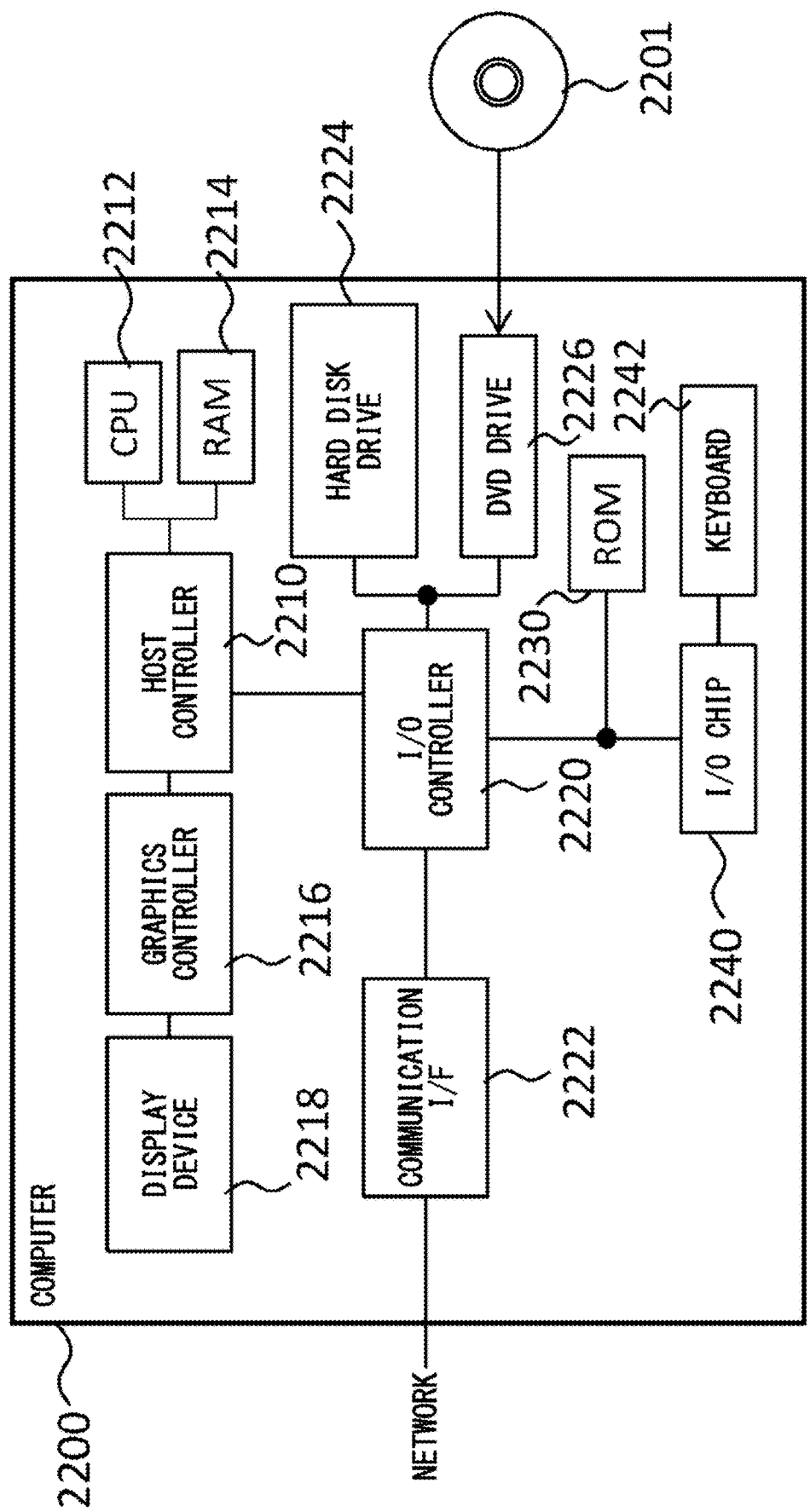
FIG. 7 illustrates an example of a computer 2200 in which aspects of the present invention may be wholly or partly embodied.

FIG. 7 illustrates an example of a computer 2200 in which aspects of the present invention may be wholly or partly embodied. A program that is installed in the computer 2200 can cause the computer 2200 to function as or perform operations associated with apparatuses of the embodiments of the present invention or one or more units thereof, and/or cause the computer 2200 to perform processes of the embodiments of the present invention or steps thereof. Such a program may be executed by a CPU 2212 to cause the computer 2200 to perform certain operations associated with some or all of the blocks of flowcharts and block diagrams described herein.

The computer 2200 according to the present embodiment includes the CPU 2212, a RAM 2214, a graphics controller 2216, and a display device 2218, which are mutually connected by a host controller 2210. The computer 2200 also includes input/output units such as a communication interface 2222, a hard disk drive 2224, a DVD-ROM drive 2226, and an IC card drive, which are connected to the host controller 2210 via an input/output controller 2220. The computer also includes legacy input/output units such as a ROM 2230 and a keyboard 2242, which are connected to the input/output controller 2220 through an input/output chip 2240.

The CPU 2212 operates according to programs stored in the ROM 2230 and the RAM 2214, thereby controlling each unit. The graphics controller 2216 obtains image data generated by the CPU 2212 on a frame buffer or the like provided in the RAM 2214 or in itself, and causes the image data to be displayed on the display device 2218.

The communication interface 2222 communicates with other electronic devices via a network. The hard disk drive 2224 stores programs and data used by the CPU 2212 within the computer 2200. The DVD-ROM drive 2226 reads the programs or the data from the DVD-ROM 2201, and provides the hard disk drive 2224 with the programs or the data via the RAM 2214. The IC card drive reads programs and data from an IC card, and/or writes programs and data into the IC card.

The ROM 2230 stores therein a boot program or the like executed by the computer 2200 at the time of activation, and/or a program depending on the hardware of the computer 2200. The input/output chip 2240 may also connect various input/output units via a parallel port, a serial port, a keyboard port, a mouse port, and the like to the input/output controller 2220.

A program is provided by computer readable media such as the DVD-ROM 2201 or the IC card. The program is read from the computer readable media, installed into the hard disk drive 2224, RAM 2214, or ROM 2230, which are also examples of computer readable media, and executed by the CPU 2212. The information processing described in these programs is read into the computer 2200, resulting in cooperation between a program and the above-mentioned various types of hardware resources. An apparatus or method may be constituted by realizing the operation or processing of information in accordance with the usage of the computer 2200.

For example, when communication is performed between the computer 2200 and an external device, the CPU 2212 may execute a communication program loaded onto the RAM 2214 to instruct communication processing to the communication interface 2222, based on the processing described in the communication program. The communication interface 2222, under control of the CPU 2212, reads transmission data stored on a transmission buffering region provided in a recording medium such as the RAM 2214, the hard disk drive 2224, the DVD-ROM 2201, or the IC card, and transmits the read transmission data to a network or writes reception data received from a network to a reception buffering region or the like provided on the recording medium.

In addition, the CPU 2212 may cause all or a necessary portion of a file or a database to be read into the RAM 2214, the file or the database having been stored in an external recording medium such as the hard disk drive 2224, the DVD-ROM drive 2226 (DVD-ROM 2201), the IC card, etc., and perform various types of processing on the data on the RAM 2214. The CPU 2212 may then write back the processed data to the external recording medium.

Various types of information, such as various types of programs, data, tables, and databases, may be stored in the recording medium to undergo information processing. The CPU 2212 may perform various types of processing on the data read from the RAM 2214, which includes various types of operations, processing of information, condition judging, conditional branch, unconditional branch, search/replace of information, etc., as described throughout this disclosure and designated by an instruction sequence of programs, and writes the result back to the RAM 2214. In addition, the CPU 2212 may search for information in a file, a database, etc., in the recording medium. For example, when a plurality of entries, each having an attribute value of a first attribute associated with an attribute value of a second attribute, are stored in the recording medium, the CPU 2212 may search for an entry matching the condition whose attribute value of the first attribute is designated, from among the plurality of entries, and read the attribute value of the second attribute stored in the entry, thereby obtaining the attribute value of the second attribute associated with the first attribute satisfying the predetermined condition.

The above-explained program or software modules may be stored in the computer readable media on the computer 2200 or near the computer 2200. In addition, a recording medium such as a hard disk or a RAM provided in a server system connected to a dedicated communication network or the Internet can be used as the computer readable media, thereby providing the program to the computer 2200 via the network.

While the present invention has been described above by way of the embodiments, the technical scope of the present invention is not limited to the range described in the above-mentioned embodiments. It is obvious to the skilled in the art that various alterations and modifications may be made to the above-mentioned embodiments. It is apparent from descriptions in the scope of claims that the technical scope of the present invention may also include a mode to which such an alteration or a modification is made.

It should be noted that an execution order for each process such as the operation, the procedure, the step, and the stage in the apparatus, the system, the program, and the method illustrated in the scope of claims, the specification, and the drawings may be realized in any order unless "ahead of", "prior to", or the like is particularly explicitly mentioned and unless the output of the previous process is used in the subsequent process. Regarding the operation flows in the scope of claims, the specification, and the drawings, even when the description is provided by using "first,", "next,", or the like for convenience, it does not mean that the execution needs to be implemented in this order.

EXPLANATION OF REFERENCES

1 apparatus, 11 training data obtaining unit, 12 training processing unit, 13 model, 14 image obtaining unit, 15 probability obtaining unit, 16 calculation unit, 17 administration condition obtaining unit, 18 detection unit, 34 training processing unit, 160 conversion unit, 2200 computer, 2201 DVD-ROM, 2210 host computer, 2212 CPU, 2214 RAM, 2216 graphics controller, 2218 display device, 2220 input/output controller, 2222 communication interface, 2224 hard disk drive, 2226 DVD-ROM drive, 2230 ROM, 2240 input/output chip, 2242 keyboard

What is claimed is:

1. An apparatus comprising:
   an image obtaining unit configured to obtain an evaluation target image depicting a subject of an evaluation target;
   a probability obtaining unit configured to obtain a recognition probability regarding the evaluation target image by using a model that outputs, in accordance with input of an image, a recognition probability at which a subject of the image is recognized as the subject before effect of a drug is expressed or the subject after the effect of the drug is expressed;
   a calculation unit configured to calculate an expression degree of the effect of the drug based on the recognition probability of the evaluation target image;
   a training data obtaining unit configured to obtain training data including a pre-expression image depicting the subject before the effect of the drug is expressed and a post-expression image depicting the subject after the effect of the drug is expressed; and
   a training processing unit configured to execute training process of the model by using the training data, wherein
   the pre-expression image is an image depicting the subject before the drug is administered, and
   the post-expression image is an image depicting the subject after the effect of the drug is expressed to a maximum extent.

2. The apparatus according to claim 1, wherein
   the probability obtaining unit obtains the recognition probability regarding each of a plurality of the evaluation target images depicting a subject to which the drug is administrated under different administration conditions, and
   the calculation unit calculates the expression degree of the evaluation target image based on the recognition probability of each of the plurality of evaluation target images.

3. The apparatus according to claim 2, further comprising:
   an administration condition obtaining unit configured to obtain administration conditions of the drug with respect to a subject of the respective evaluation target images; and
   a detection unit configured to detect an administration condition under which the expression degree becomes a predetermined summary statistic based on the expression degrees of the respective evaluation target images and the administration conditions corresponding to the respective evaluation target images.

4. The apparatus according to claim 1, wherein
   the probability obtaining unit obtains the recognition probability regarding each of a plurality of evaluation target images depicting a subject to which the drug is administrated under a uniform administration condition, and
   the calculation unit calculates the expression degree based on a representative value of a plurality of the recognition probabilities regarding the plurality of evaluation target images.

5. The apparatus according to claim 1, wherein
   the probability obtaining unit obtains the recognition probability regarding each of a plurality of evaluation target images depicting a subject to which the drug is administrated under a uniform administration condition, and
   the calculation unit calculates the expression degree based on a variance of a plurality of the recognition probabilities regarding the plurality of evaluation target images.

6. The apparatus according to claim 1,
   wherein the calculation unit includes a conversion unit configured to convert the recognition probability regarding the evaluation target image into the expression degree.

7. A computer-implemented method comprising:
obtaining, by a computer, an evaluation target image depicting a subject of an evaluation target;
obtaining, by the computer, a recognition probability regarding the evaluation target image by using a model that outputs, in accordance with input of an image, a recognition probability at which a subject of the image is recognized as the subject before effect of a drug is expressed or the subject after the effect of the drug is expressed;
calculating, by the computer, an expression degree of the effect of the drug based on the recognition probability of the evaluation target image;
obtaining, by the computer, training data including a pre-expression image depicting the subject before the effect of the drug is expressed and a post-expression image depicting the subject after the effect of the drug is expressed; and
executing, by the computer, training process of the model by using the training data, wherein
the pre-expression image is an image depicting the subject before the drug is administered, and
the post-expression image is an image depicting the subject after the effect of the drug is expressed to a maximum extent.

8. A computer-readable recording medium having recorded thereon a program that, when executed by a computer, causes the computer to perform operations comprising:

obtaining an evaluation target image depicting a subject of an evaluation target;
obtaining a recognition probability regarding the evaluation target image by using a model that outputs, in accordance with input of an image, a recognition probability at which a subject of the image is recognized as the subject before effect of a drug is expressed or the subject after the effect of the drug is expressed, and obtaining a recognition probability regarding the evaluation target image;
calculating an expression degree of the effect of the drug based on the recognition probability of the evaluation target image;
obtaining training data including a pre-expression image depicting the subject before the effect of the drug is expressed and a post-expression image depicting the subject after the effect of the drug is expressed; and
executing training process of the model by using the training data, wherein
the pre-expression image is an image depicting the subject before the drug is administered, and
the post-expression image is an image depicting the subject after the effect of the drug is expressed to a maximum extent.

* * * * *